US00PP24938P2

(12) United States Plant Patent
Eveleens

(10) Patent No.: US PP24,938 P2
(45) Date of Patent: Sep. 30, 2014

(54) ***GERBERA* PLANT NAMED 'GARVIVIAN IMPROVED'**

(50) Latin Name: *Gerbera hybrida*
Varietal Denomination: Garvivian Improved

(71) Applicant: Jan Leendert Eveleens, Aalsmeer (NL)

(72) Inventor: Jan Leendert Eveleens, Aalsmeer (NL)

(73) Assignee: Florist Holland B.V., Aalsmeer (NL)

( * ) Notice: Subject to any disclaimer, the term of this patent is extended or adjusted under 35 U.S.C. 154(b) by 85 days.

(21) Appl. No.: 13/694,556

(22) Filed: Dec. 12, 2012

(51) Int. Cl.
*A01H 5/00* (2006.01)

(52) U.S. Cl.
USPC ..... Plt./357

(58) Field of Classification Search
USPC ..... Plt./357
See application file for complete search history.

*Primary Examiner* — Annette Para
(74) *Attorney, Agent, or Firm* — C. A. Whealy

(57) ABSTRACT

A new and distinct cultivar of *Gerbera* plant named 'Garvivian Improved', characterized by its compact, broadly upright and uniformly mounding plant habit; numerous narrowly obovate leaves per plant, dense and bushy appearance; numerous inflorescences with narrowly oblanceolate pale yellow-colored ray florets; upright and strong scapes; and good garden performance.

1 Drawing Sheet

Botanical designation: *Gerbera hybrida.*
Cultivar denomination: 'GARVIVIAN IMPROVED'.

BACKGROUND OF THE INVENTION

The present invention relates to a new and distinct cultivar of *Gerbera* plant, botanically known as *Gerbera hybrida* and hereinafter referred to by the name 'Garvivian Improved'.

The new *Gerbera* plant is a product of a planned breeding program conducted by the Inventor in De Kwakel, The Netherlands. The objective of the breeding program is to create new compact container *Gerbera* plants with numerous inflorescences, good garden performance, frost tolerance and attractive inflorescence coloration.

The new *Gerbera* plant is a naturally-occurring whole plant mutation of *Gerbera hybrida* 'Garvivian', not patented. The new *Gerbera* plant was discovered and selected by the Inventor as a single flowering plant within a population of plants of 'Garvivian' in a controlled greenhouse environment in De Kwakel, The Netherlands in March, 2010.

Asexual reproduction of the new *Gerbera* plant by cuttings and by tissue culture in a controlled environment in De Kwakel, The Netherlands since September, 2010 has shown that the unique features of this new *Gerbera* plant are stable and reproduced true to type in successive generations.

SUMMARY OF THE INVENTION

Plants of the new *Gerbera* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Garvivian Improved'. These characteristics in combination distinguish 'Garvivian Improved' as a new and distinct *Gerbera* plant:

1. Compact, broadly upright and uniformly mounding plant habit.

2. Numerous narrowly obovate leaves per plant, dense and bushy appearance.
3. Numerous inflorescences with narrowly oblanceolate pale yellow-colored ray florets.
4. Upright and strong scapes.
5. Good garden performance; relatively tolerant to rain, wind and low temperatures.

Plants of the new *Gerbera* differ from plants of the parent, 'Garvivian', in the following characteristics:

1. Plants of the new *Gerbera* are more vigorous than plants of 'Garvivian'.
2. Plants of the new *Gerbera* have larger leaves than plants of 'Garvivian'.
3. Plants of the new *Gerbera* have larger inflorescences than plants of 'Garvivian'.

Plants of the new *Gerbera* can be compared to plants of the *Gerbera hybrida* 'Summer', disclosed in U.S. Plant Pat. No. 22,387. Plants of the new *Gerbera* differ from plants of 'Summer' in the following characteristics:

1. Plants of the new *Gerbera* and 'Summer' differ in leaf shape as plants of 'Summer' have oblong-shaped leaves.
2. Plants of the new *Gerbera* have larger inflorescences than plants of 'Summer'.
3. Plants of the new *Gerbera* and 'Summer' differ in ray floret color as plants of 'Summer' have intense yellow-colored ray florets.

BRIEF DESCRIPTION OF THE PHOTOGRAPH

The accompanying photograph illustrates the overall appearance of the new *Gerbera* plant showing the colors as true as it is reasonably possible to obtain in colored reproductions of this type. Colors in the photograph may differ slightly from the color values cited in the detailed botanical description which accurately describe the colors of the new *Gerbera* plant. The photograph comprises a side perspective view of a typical flowering plant of 'Garvivian Improved' grown in a container.

DETAILED BOTANICAL DESCRIPTION

The aforementioned photograph and following observations and measurements describe plants grown during the late winter and early spring in 14-cm containers in a glass-covered greenhouse in De Kwakel, The Netherlands and under cultural practices typical of commercial container *Gerbera* production. During the production of the plants, day temperatures ranged from 10° C. to 20° C. and night temperatures ranged from 10° C. to 15° C. Rooted young tissue-cultured plants were five months old when the photograph was taken and six months old when the description was taken. In the following description, color references are made to The Royal Horticultural Society Colour Chart, 2007 edition, except where general terms of ordinary dictionary significance are used.

Botanical classification: *Gerbera hybrida* 'Garvivian Improved'.

Parentage: Naturally-occurring whole plant mutation of *Gerbera hybrida* 'Garvivian', not patented.

Propagation:

*Type*.—By tissue culture.

*Time to initiate roots, summer and winter*.—About 2.5 to 3 weeks at temperatures of 20° C.

*Time to produce a rooted young plant, summer and winter*.—About five to six weeks at temperatures of 20° C. to 26° C.

*Root description*.—Fibrous; white in color.

Plant description:

*Appearance*.—Herbaceous perennials that are typically grown as container or garden plants; compact and uniformly mounding plant habit, broadly upright and roughly globular in shape; numerous leaves arranged in basal rosettes and outwardly arching; dense and bushy habit; inflorescences held above the foliar plane on erect and strong basal scapes; moderately vigorous growth habit.

*Plant height, soil level to top of foliar plane*.—About 20 cm.

*Plant height, soil level to top of inflorescences*.—About 29 cm.

*Plant width*.—About 38.2 cm.

Foliage description:

*Arrangement*.—Alternate, simple.

*Length*.—About 14.1 cm.

*Width*.—About 6.3 cm.

*Shape*.—Narrowly obovate; runcinate.

*Apex*.—Obtuse to broadly acute.

*Base*.—Acuminate.

*Margin*.—Coarsely and irregularly angulate; undulate; sinuses divergent.

*Texture, upper surface*.—Moderately pubescent.

*Texture, lower surface*.—Densely tomentose.

*Venation pattern*.—Pinnate.

*Color*.—Developing leaves, upper surface: Darker than between 141A and 143A. Developing leaves, lower surface: Close to 138B. Fully expanded leaves, upper surface: Between N137A and 147A; venation, close to 144A. Fully expanded leaves, lower surface: Between 137D and 191A; venation, close to 143B.

*Petioles*.—Length: About 9.1 cm. Diameter: About 3 mm. Texture, upper surface: Sparsely pubescent. Texture, lower surface: Moderately to densely pubescent. Color, upper surface: Close to 144A. Color, lower surface: Close to 144A to 144B.

Inflorescence description:

*Appearance*.—Composite inflorescence form with narrowly oblanceolate-shaped ray florets; solitary inflorescences borne on upright and strong scapes above the foliar plane; ray and disc florets arranged acropetally on a capitulum.

*Fragrance*.—None detected.

*Flowering season*.—Plants begin flowering about three months after planting; plants flower from late winter to late summer in The Netherlands under outdoor nursery conditions; plants flower year-round under greenhouse conditions.

*Inflorescence longevity*.—Depending on the temperature, inflorescences last about two to four weeks on the plant; inflorescences not persistent.

*Quantity of inflorescences*.—Freely flowering habit with about 20 open and developing inflorescences per plant at one time.

*Inflorescence buds*.—Height: About 1.7 cm. Diameter: About 1.8 cm. Shape: Globular. Color: Close to 143A; towards the apex, close to 176C.

*Inflorescence size*.—Diameter: About 6.5 cm. Depth (height): About 2.3 cm. Diameter of disc: About 2.2 cm. Receptacle height: About 3 mm. Receptacle diameter: About 3 mm. Receptacle color: Close to 193B to 193C.

*Ray florets*.—Orientation: About 70° from vertical. Length: About 3.5 cm. Width: About 7 mm. Shape: Narrowly oblanceolate. Apex: Obtuse. Base: Cuneate. Margin: Entire. Texture, upper and lower surfaces: Smooth, glabrous; slightly velvety; slightly longitudinally ridged. Number per inflorescence: About 40 arranged in two whorls. Color: When opening, upper surface: Close to 7B and 8A. When opening, lower surface: Close to 35C tinged with close to 53B. Fully opened, upper surface: Close to 8C; color does not fade with development. Fully opened, lower surface: Close to 31C to 31D tinged with close to 39B; color does not fade with development.

*Disc florets*.—Arrangement: Massed at center of receptacle. Shape: Tubular. Apex: Acute. Base: Lower 80%, fused. Margin: Entire. Length: About 1.1 cm. Width: About 3 mm. Texture, upper and lower surfaces: Smooth, glabrous. Number of disc florets per inflorescence: About 120. Color, prior to opening: Apex: Close to 150D. Mid-section: Close to 14D. Base: Close to 145C. Color, when opening and fully opened: Apex: Close to 8C. Mid-section: Close to 8D. Base: Close to 157D.

*Pappus*.—Quantity of hairs per floret: About 50. Length: About 6 mm. Diameter: Less than 1 mm. Texture: Soft. Color: Close to 160D.

*Phyllaries*.—Number of phyllaries per inflorescence: About 60 arranged in three whorls. Length: About 1.3 cm. Width: About 2 mm. Shape: Lanceolate. Apex: Narrowly acute. Base: Cuneate. Margin: Entire. Texture, upper surface: Smooth, glabrous. Texture, lower surface: Densely tomentose. Color, upper surface: Close to 143B. Color, lower surface: Close to 137B to 137C.

*Scapes*.—Length: About 22.6 cm. Diameter: About 4 mm; distally, about 3 mm. Angle: About 10° from vertical. Strength: Strong. Texture: Densely tomentose. Color: Close to 144A; distally, close to 147A.

*Reproductive organs*.—Androecium: Quantity per floret: Two. Filament length: About 6 mm. Filament color: Close to 155A. Anther shape: Lanceolate. Anther length: About 4 mm. Anther color: Close to 10A. Pollen amount: Scarce. Pollen color: Close to 12B. Gynoecium: Quantity per floret: One. Pistil length: About 1.1 cm. Stigma shape: Cleft. Stigma color: Close to NN155C to NN155D. Style length: About 9 mm. Style color: Close to N155B to N155C. Ovary color: Close to 145C.

*Seeds and fruits*.—Seed and fruit production has not been observed on plants of the new *Gerbera*.

Disease & pest resistance: Resistance to pathogens and pests common to *Gerbera* plants has not been observed on plants of the new *Gerbera* grown under commercial production conditions.

Garden performance: Plants of the new *Gerbera* have been observed to have good garden performance and to be relatively tolerant to wind and rain and to tolerant temperatures ranging from about −5° C. to about 35° C.

It is claimed:

1. A new and distinct *Gerbera* plant named 'Garvivian Improved' as illustrated and described.

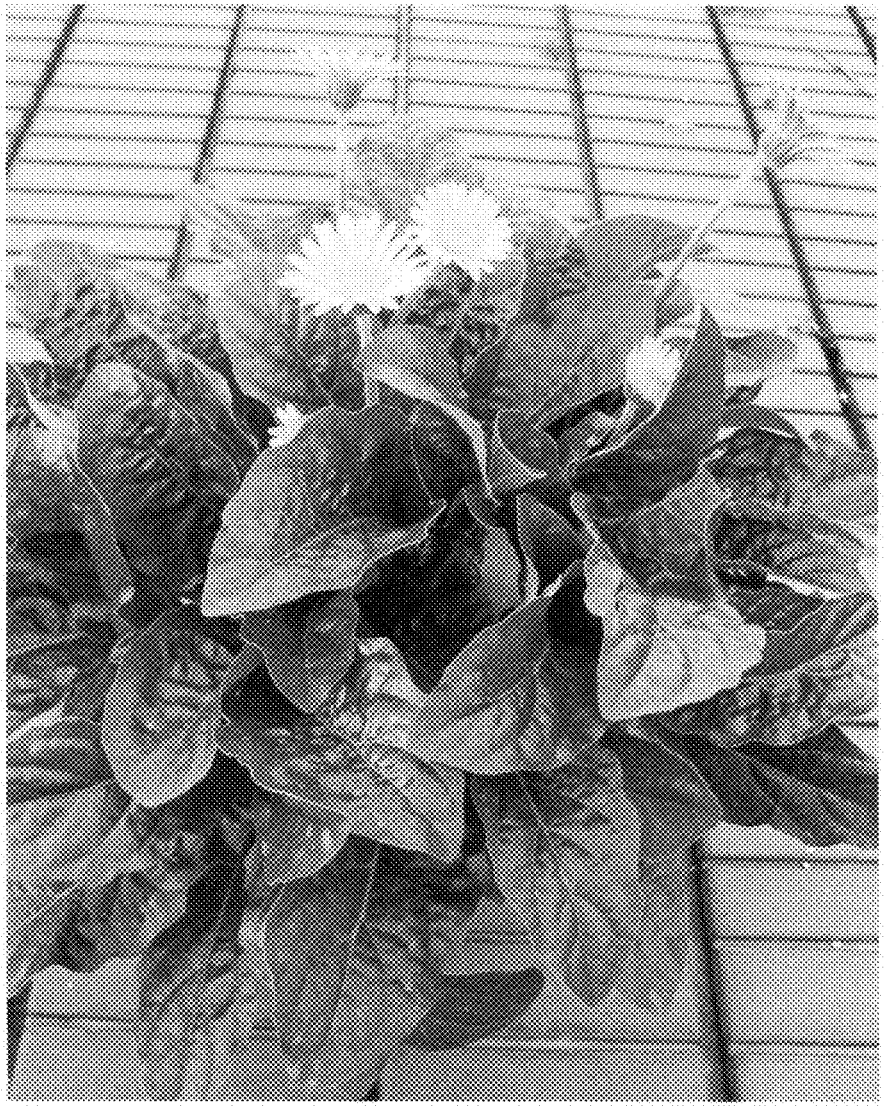

* * * * *